(12) United States Patent
Sasing et al.

(10) Patent No.: US 8,337,499 B2
(45) Date of Patent: Dec. 25, 2012

(54) SURGICAL CUTTING DEVICES AND METHODS

(75) Inventors: Jude L. Sasing, Quezon (PH); Joseph A. Garcia, Quezon (PH); Roberto R. Fresnido, Rizal (PH); Ramon B. Gustilo, Eden Prairie, MN (US)

(73) Assignee: Dgimed Ortho, Inc., Minnetonka, MN (US)

( * ) Notice: Subject to any disclaimer, the term of this patent is extended or adjusted under 35 U.S.C. 154(b) by 1244 days.

(21) Appl. No.: 11/980,208

(22) Filed: Oct. 30, 2007

(65) Prior Publication Data

US 2008/0114365 A1 May 15, 2008

Related U.S. Application Data

(60) Provisional application No. 60/855,325, filed on Oct. 30, 2006.

(51) Int. Cl.
*A61B 17/00* (2006.01)

(52) U.S. Cl. .......................................................... 606/80

(58) Field of Classification Search .................... 606/79, 606/80, 167, 168, 170–172
See application file for complete search history.

(56) References Cited

U.S. PATENT DOCUMENTS

| | | | |
|---|---|---|---|
| 4,926,860 A | 5/1990 | Stice et al. | |
| 5,035,712 A | 7/1991 | Hoffman | |
| 5,067,489 A | 11/1991 | Lind | |
| 5,330,468 A | 7/1994 | Burkhart | |
| 5,690,660 A | 11/1997 | Kauker et al. | |
| 5,695,513 A | 12/1997 | Johnson et al. | |
| 5,895,389 A | 4/1999 | Schenk et al. | |
| 6,063,095 A | 5/2000 | Wang et al. | |
| 6,068,642 A | 5/2000 | Johnson et al. | |
| 6,309,392 B1 | 10/2001 | Alexander et al. | |
| 6,342,057 B1 | 1/2002 | Brace et al. | |
| 6,746,451 B2 | 6/2004 | Middleton et al. | |
| 2003/0018270 A1 | 1/2003 | Makin et al. | |
| 2003/0220646 A1* | 11/2003 | Thelen et al. | 606/79 |

FOREIGN PATENT DOCUMENTS

| | | |
|---|---|---|
| WO | WO 97/31577 | 9/1997 |
| WO | WO 2004/043271 | 5/2004 |

OTHER PUBLICATIONS

Chinese Office Action from corresponding patent application; dated May 12, 2010; 9 pages.
Singapore Office Action / Written Opinion from corresponding application (prepared by Australian Patent Office); dated Dec. 21, 2009; 8 pages.

* cited by examiner

*Primary Examiner* — Anu Ramana
(74) *Attorney, Agent, or Firm* — Barbara A. Wrigley; Oppenheimer Wolff & Donnelly, LLP

(57) ABSTRACT

The present invention provides surgical drilling devices and methods. An exemplary surgical drilling device in accordance with the present invention comprises a housing, a retractable guide tube assembly, and a flexible cable drill. The retractable guide tube assembly comprises an arcuate guide tube slidingly positioned in a first arcuate channel of the housing. The arcuate guide tube is operatively connected to an actuating rod slidingly positioned in a second channel of the housing wherein the actuating rod controllably advances and retracts the arcuate guide tube. The flexible cable drill comprises a first portion slidingly positioned in the arcuate guide tube and a second portion slidingly positioned in a third channel of the housing.

18 Claims, 10 Drawing Sheets

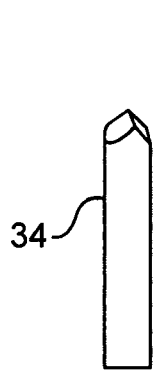
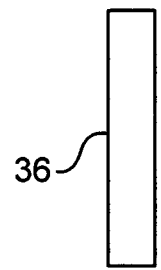
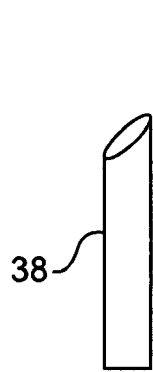
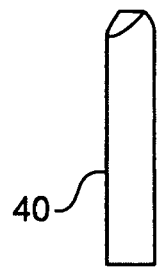
Fig. 10a   Fig. 10b   Fig. 10c   Fig. 10d
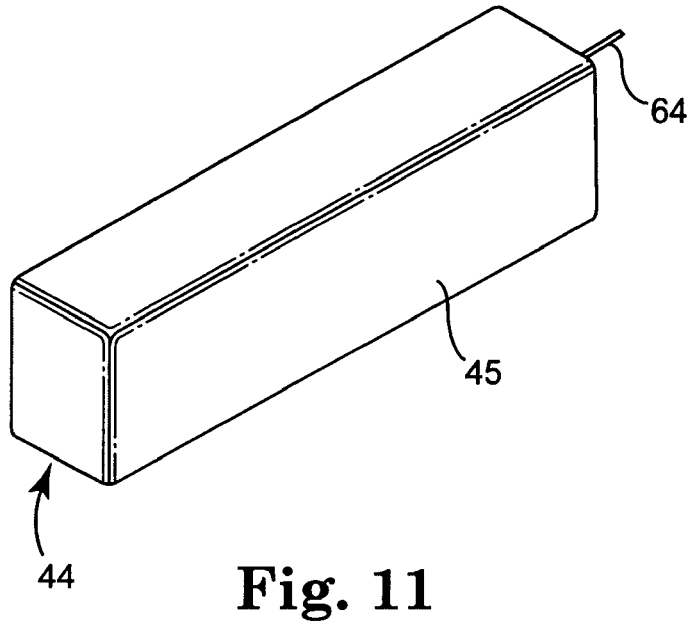
Fig. 11
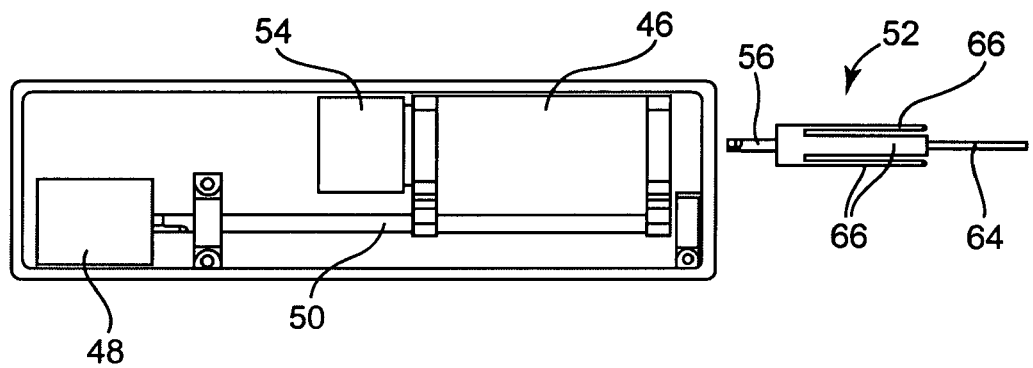
Fig. 14

SURGICAL CUTTING DEVICES AND METHODS

CROSS REFERENCE TO RELATED APPLICATIONS

The present application claims priority to U.S. Provisional Application No. 60/855,325 filed Oct. 30, 2006, the entire contents of which is incorporated herein by reference for all purposes.

TECHNICAL FIELD

The present invention relates to flexible cutting tools and more particularly for cutting tools and methods used in surgical procedures.

BACKGROUND

Surgical procedures often require the cutting or drilling of holes or channels into bone, teeth, or soft tissue, such as can be used for securing components made of metal or other materials to the bone of a patient. For example, these holes may be used to receive screws, sutures, or bone anchors, thereby allowing for implants or other devices to be secured to the bone, or to provide for reattachment of ligaments or tendons to a bone. A number of different surgical drilling devices are available for this purpose, many of which include a motor and a drill bit that can provide a hole of the desired depth and diameter. An example of such a device is described in U.S. Pat. No. 5,695,513 to Johnson et al. and International Publication No. WO97/32577 to Johnson et al., the disclosures of which are incorporated by reference herein for all purposes. The Johnson et al. references describe a flexible cutting instrument that is formed through the use of a helically wound cable made of a metal such as nitinol or another superelastic alloy. In this device, the cable is bent to a predetermined bend radius and rotated in a direction that tends to tighten the helically wound fibers of the cable. Drilling with this device is performed while continuously maintaining the cutting means at least partially within the hole being drilled and advancing the cable through its holder. Devices of this type can provide sufficient drilling capabilities for many situations; however, there is a continued need for additional surgical drilling tools and methods for certain surgical procedures and situations.

SUMMARY

The present invention provides surgical drilling devices having a flexible cable drill and a retractable arcuate guide tube. A retractable arcuate guide tube for a flexible cable drill allows the use of a large bend radius for the cable drill and allows the cable drill to be deployed inside the limited space of the inner cavity of an intramedullary nail during a surgical procedure. A large bend radius for the cable drill helps to maximize the lifetime of the cable drill. Having a retractable guide tube with a flexible cable drill advantageously helps to reduce the chances of the cable drill breaking inside a bone during a surgical procedure.

Surgical drilling in accordance with the present invention utilizes a flexible cable drill cable that is advanced axially through a retractable arcuate guide tube during the drilling process. Plural portions of the cable drill are advantageously exposed to the arcuate guide tube throughout the process. In an exemplary embodiment of the present invention, the cable drill is preferably advanced at a rate wherein the cable drill spends less revolutions in the arcuate guide tube than the life of the cable drill for a particular bend radius (as measured in number of revolutions). If desired, each point on the cable drill can experience a dwell time in the arcuate guide tube that is less than the life of the cable drill for a particular bend radius (as measured in terms of time at a given rpm).

In an aspect of the present invention, a surgical drilling device is provided. The surgical drilling device comprises a housing, a retractable guide tube assembly, and a flexible cable drill. The retractable guide tube assembly comprises an arcuate guide tube slidingly positioned in a first arcuate channel of the housing. The arcuate guide tube is operatively connected to an actuating rod slidingly positioned in a second channel of the housing wherein the actuating rod controllably advances and retracts the arcuate guide tube. The flexible cable drill comprises a first portion slidingly positioned in the arcuate guide tube and a second portion slidingly positioned in a third channel of the housing.

In another aspect of the present invention, another surgical drilling device is provided. The surgical drilling device comprises a housing, a retractable guide tube assembly, and a flexible cable drill. The housing comprises an internal channel having a first arcuate portion and a second linear portion. The retractable guide tube assembly comprises an arcuate guide tube slidingly positioned in the arcuate portion of the channel of the housing. An end of the arcuate guide tube is operatively connected to an end of an actuating tube slidingly positioned in the linear portion of the channel of the housing. The flexible cable drill comprises a first portion slidingly positioned in the arcuate guide tube and a second portion slidingly positioned in the actuating tube.

In another aspect of the present invention, a drive system for a surgical drilling device is provided. The drive system comprises a housing, first and second motors, a disposable drive coupling, and a load cell. The first motor comprises a drive shaft operatively coupled to a lead screw. The first motor and lead screw are mounted in the housing. The second motor comprises a body portion and a drive shaft wherein the body portion is attached to the lead screw so the second motor is translatable along a linear path as driven by the lead screw. The disposable drive coupling is releasably engaged with the body portion of the second motor. The disposable drive coupling includes a drive shaft releasably coupled with the drive shaft of the second motor. The load cell is operatively positioned relative to the disposable drive coupling for sensing axial forces acting on the drive shaft of the disposable drive coupling.

In yet another aspect of the present invention a method for drilling bone is provided. The method comprising the steps of providing a surgical drilling device comprising a housing and a cable drill slidingly positioned in an arcuate retractable guide tube, the cable drill comprising a cutting end; slidingly advancing the arcuate retractable guide tube; positioning the cutting end of the cable drill relative to bone; rotating the cable drill; and slidingly advancing the cable drill through the arcuate retractable guide tube.

BRIEF DESCRIPTION OF THE DRAWINGS

The present invention will be further explained with reference to the appended Figures, wherein like structure is referred to by like numerals throughout the several views, and wherein:

FIGS. 10a-10d are side views of exemplary cutting edges that can be used for the distal or drilling end of a flexible cable drill in accordance with the present invention;

FIG. 11 is a perspective view of an exemplary cable drill drive in accordance with the present invention;

FIG. 14 is a side view of the cable drill drive of FIGS. 11 and 12 showing the disposable drive coupling removed from the drill drive;

DETAILED DESCRIPTION

Figure 1:
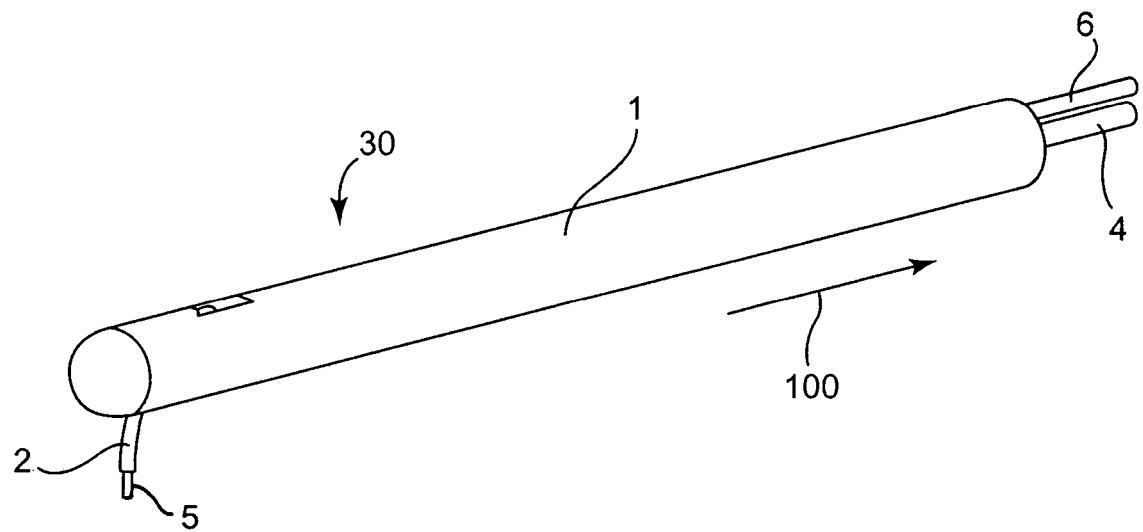
FIG. 1 is a perspective view of an exemplary surgical drilling device having an arcuate retractable guide tube in accordance with the present invention.
Figure 2:
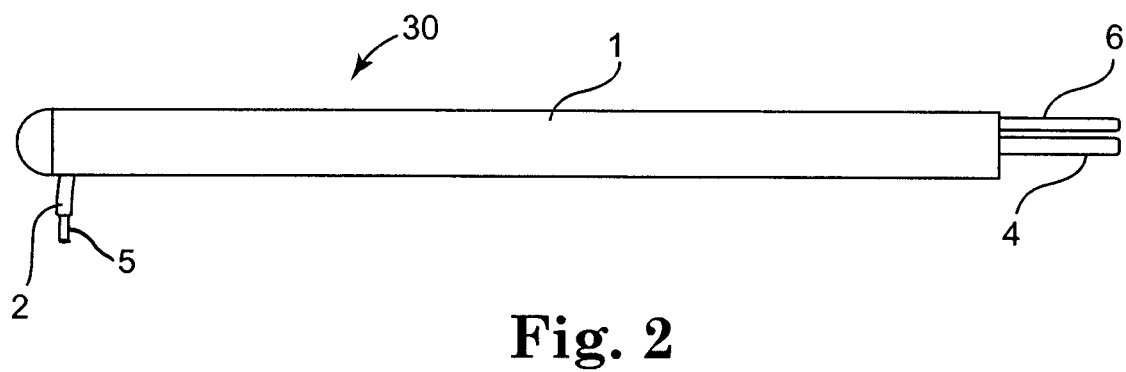
FIG. 2 is a side view of the surgical drilling device of FIG. 1.
Figure 3:
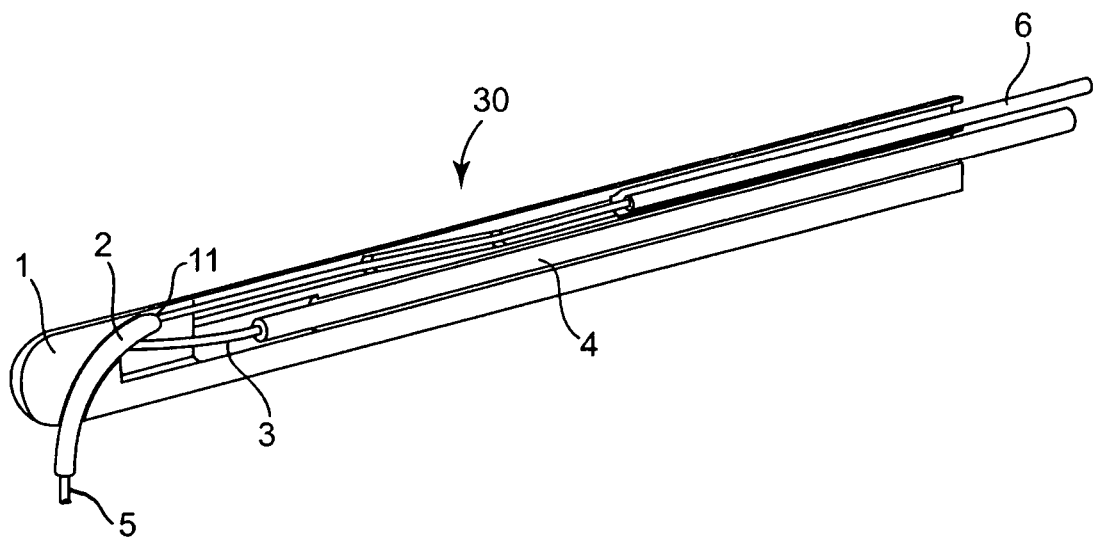
FIG. 3 is a cross-sectional perspective view of the surgical drilling device of FIG. 1.
Figure 4:
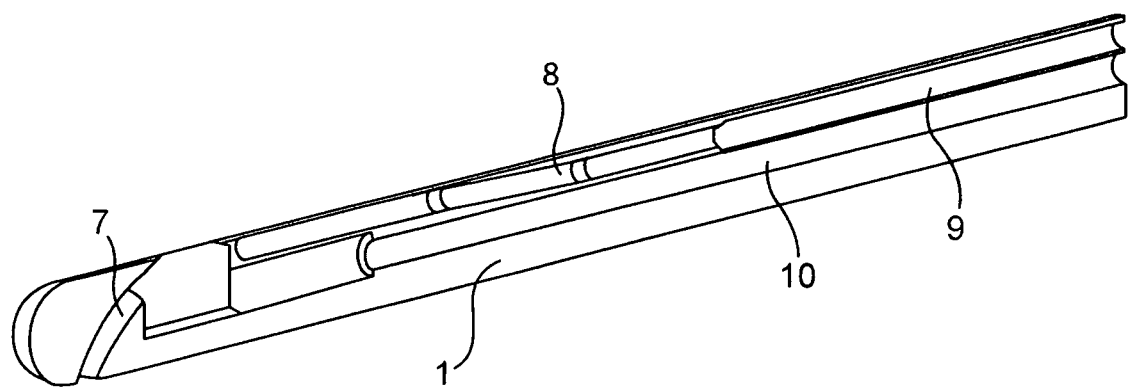
FIG. 4 is a cross-sectional perspective view of a housing of the surgical drilling device of FIG. 1.

Referring now to the Figures, wherein the components are labeled with like numerals throughout the several Figures, and initially to FIGS. 1-3, a preferred configuration of a surgical drilling device 30 comprising a retractable cable guide assembly in accordance with the present invention is illustrated. The device 30, as shown, generally includes a housing 1, a retractable guide tube 2, a flexible coupling 3, a push rod 4, a cable drill 5, and a cable carrier 6. Housing 1, as shown, is generally cylindrical and comprises cavities 7, 8, 9, and 10 which can be seen in the cutaway view of FIG. 4. Cavity 7 can be shaped generally like a section of a torus, for example, and is used for slidingly guiding the retractable guide tube 2. The torus shape functions to slidingly guide the retractable guide tube 2 (which can also be similarly shaped like a section of a torus) without having to provide a pin joint to act as a pivot point. That is, such a pivot point would typically need to be located outside the housing 1 in order to have a large radius guide tube 2 fit inside the confines of housing 1. A pin joint outside housing 1 is undesirable because such assembly would not fit inside the cavity of an intramedullary nail. With the generally torus shaped cavity 7, however, it is advantageously possible to have the pivot point outside the housing 1 without having to provide a physical point outside housing 1 for such a purpose.

Housing 1 further includes an elongated cavity 8 that is sized for slidingly guiding and supporting cable drill 5. Yet another cavity 9, which is axially adjacent to cavity 8, is used for slidingly guiding cable carrier 6, and a cavity 10 is sized for slidingly guiding push rod 4.

Figure 5:
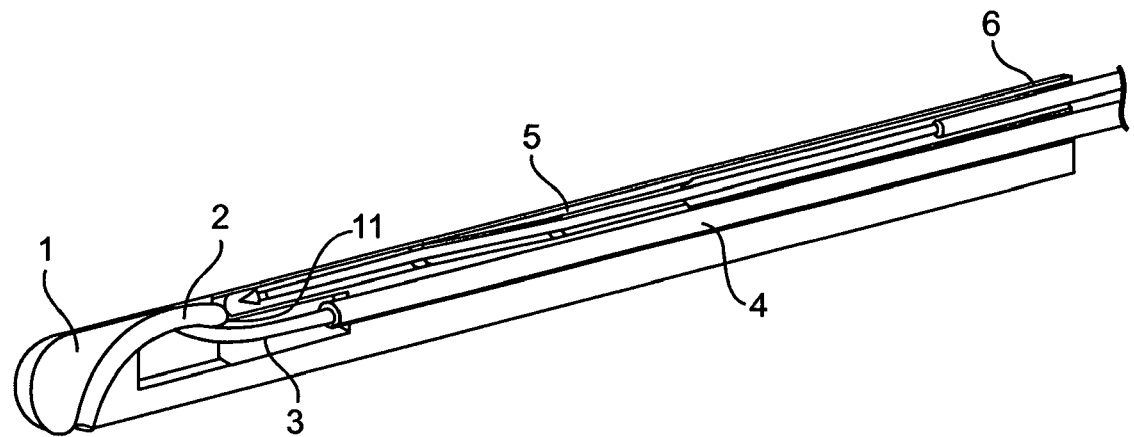
FIG. 5 is a cross-sectional perspective view of the surgical drilling device of FIG. 1, showing in particular an arcuate guide tube in a retracted position.

In order to insert the device 30 into the cavity of an intramedullary nail, push rod 4 is pulled in the direction indicated by reference numeral 100, causing flexible coupling 3 to pull retractable guide tube 2 into housing 1, as shown in FIG. 5. Once the device 30 is properly positioned inside an intermedullary nail, push rod 4 is pushed in the opposite direction causing flexible coupling 3 to push retractable guide tube 2 out of housing 1 as shown in FIG. 3. In this position, an end 11 of retractable guide tube 2 becomes aligned with cavity 8 of housing 1, thereby allowing cable drill 5 to be advanced from cavity 8 into retractable guide tube 2, as shown in FIG. 3.

Figure 6:
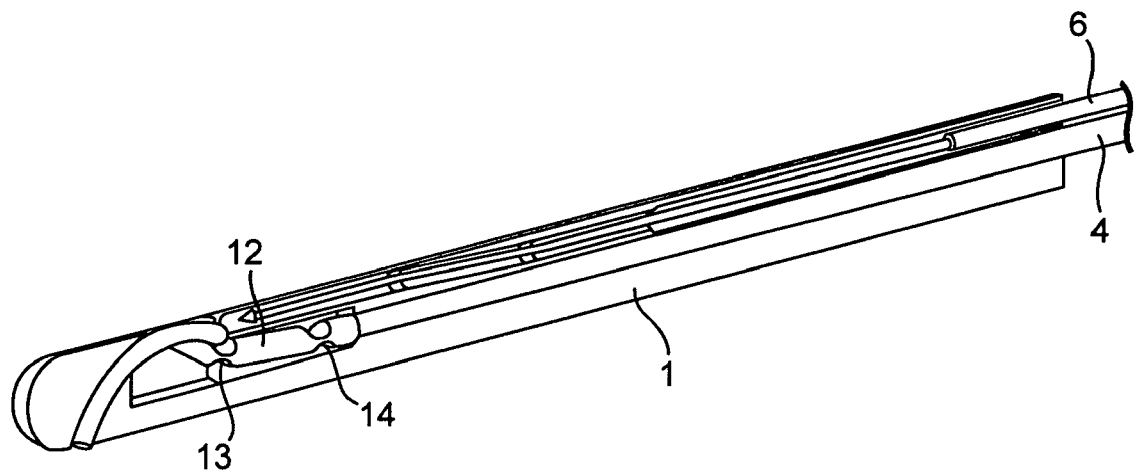
FIG. 6 is a cross-sectional perspective view of another exemplary surgical drilling device having an arcuate retractable guide tube in accordance with the present invention.

Flexible coupling 3 is designed to be sufficiently flexible to allow retractable guide tube 2 to rotate and/or slide within cavity 7. In one exemplary embodiment, the flexible coupling comprises a hinged coupling 12, as shown in FIG. 6. Hinged coupling 12 includes first and second spaced apart hinges 13 and 14, respectively, which can comprise thinned sections of hinged coupling 12, as illustrated, or any other desired device or mechanism that functions as a hinge such as pin jointed hinges, for example. Any number of hinge regions can be used.

Figure 7:
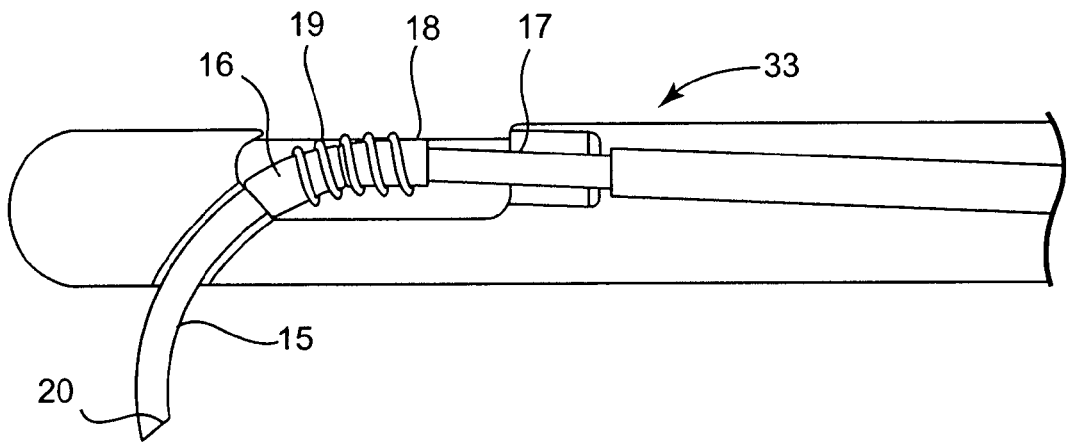
FIG. 7 is cross-sectional view of yet another exemplary surgical drilling device having an arcuate guide tube in accordance with the present invention.
Figure 8:
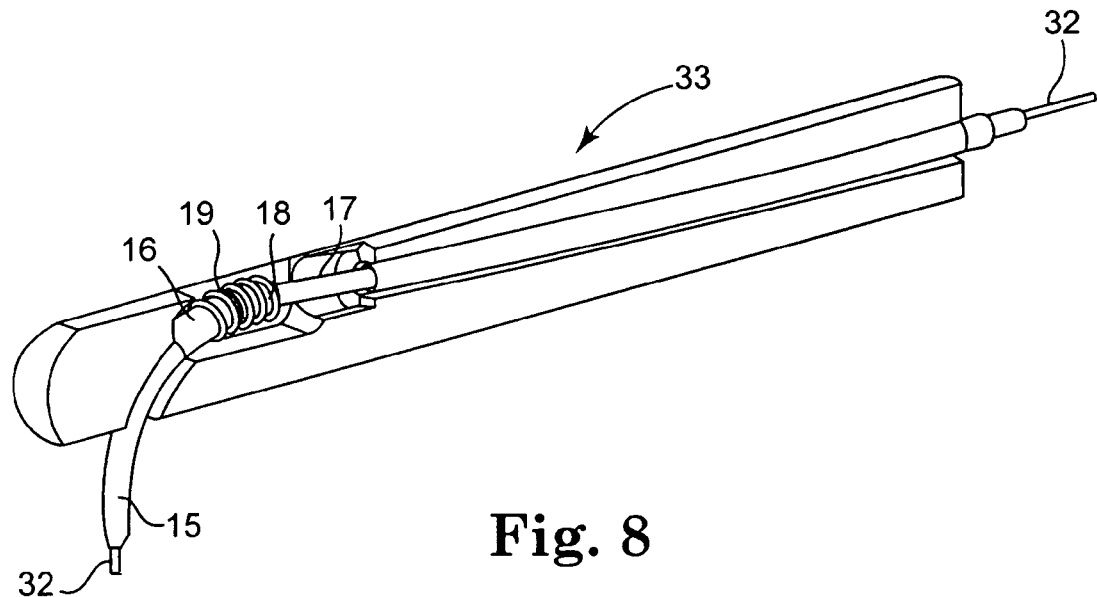
FIG. 8 is a partial cross-sectional perspective view of the surgical drilling device of FIG. 7, showing in particular an arcuate guide tube in an extended position and a cable drill extended from the arcuate guide tube.
Figure 9:
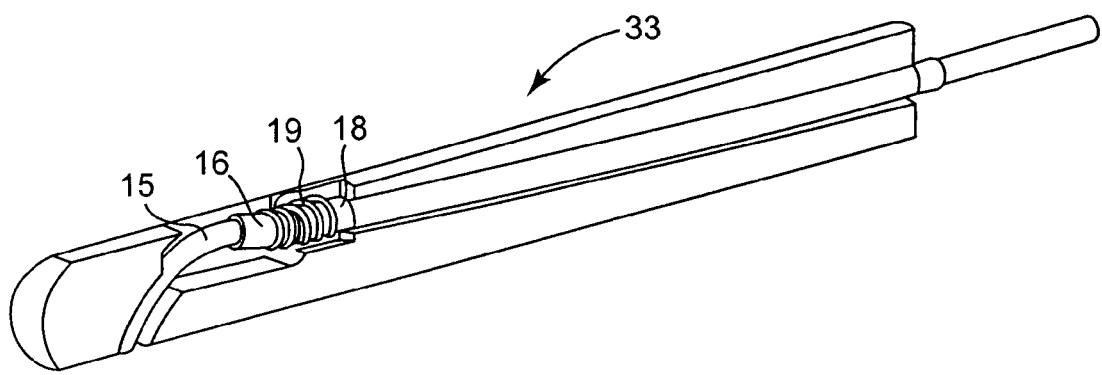
FIG. 9 is a partial cross-sectional perspective view of the surgical drilling device of FIG. 7, showing in particular an arcuate guide tube in a retracted position.

Another exemplary embodiment of a surgical drilling device 33 comprising a retractable cable guide assembly in accordance with the present invention is illustrated in FIGS. 7, 8, and 9. In this embodiment, a retractable guide tube 15 has an enlarged end portion 16. An actuating tube 17 also has an enlarged end portion 18. The enlarged end portions 16 and 18 provide a large abutting surface contact between guide tube 15 and actuating tube 17 which allows contact even if there is misalignment between guide tube 15 and actuating tube 17, such as when guide tube 15 is in the retracted position. The enlarged end portion 16 also acts as a funnel to guide cable drill 32 if there is misalignment between guide tube 15 and actuating tube 17. Actuating tube 17 is used to push guide tube 15 to an extended position, and at the same time also acts as the cable guide. In this way, when in the extended position shown in FIG. 8, cable drill 32 goes through actuating tube 17 and into guide tube 15.

In the extended position shown in FIG. 7, the enlarged end portion 18 of actuating tube 17 is abutting or pushing against enlarged end portion 16 of guide tube 15. During retraction of guide tube 15, the cable drill 32 is first pulled out of the device along the direction indicated by reference numeral 31 in FIG.

8, and then actuating tube 17 is pulled in the same direction. This causes coil spring 19 to be pulled together with actuating tube 17. Coil spring 19 in turn pulls guide tube 15, causing it to retract as shown in FIG. 9. The flexibility of coil spring 19 accommodates misalignment that may occur between respective ends of guide tube 15 and actuating tube 17 during retraction due to guide tube 15 and actuating tube 17 following different trajectories during retraction.

During extension of guide tube 15, actuating tube 17 is pushed in the direction opposite to direction 31. The force from actuating tube 17 is transmitted to guide tube 15 primarily through enlarged portion 16 and secondarily through coil spring 19. As actuating tube 17 is being pushed in the direction opposite to direction 31, enlarged portion 16 of guide tube 15 gradually becomes aligned with enlarged portion 18 of actuating tube 17. In an alternative configuration, coil spring 19 can be replaced with a suitable flexible element or portion that can take up tensional loads while also providing some ability to move sideways. One example of this would be a sleeve made of cloth or other materials.

The tip of guide tube 15 preferably includes a sharp edge 20 that can help to cut into cancellous bone. This configuration is particularly advantageous when guide tube 15 protrudes outside an intramedullary nail during extension. This allows guide tube 15 to be fully extended and also stabilizes guide tube 15 in the cancellous bone.

Figure 21:
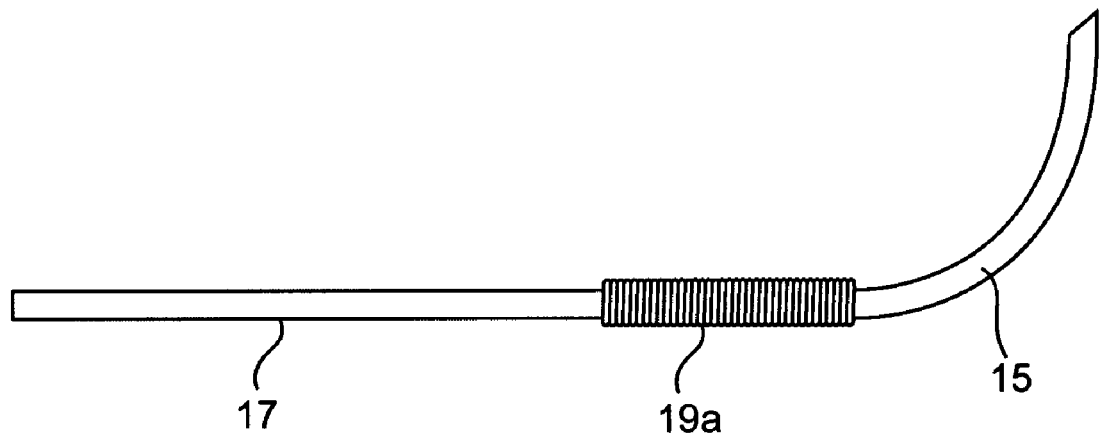
FIG. 21 is a schematic view of another exemplary surgical drilling device in accordance with the present invention.

In another exemplary embodiment of the present invention, guide tube 15 and actuating tube 17 are connected by a tightly wound extension spring 19a that can take up compressive loads (i.e., it does not compress), but is still flexible to deform sideways to accommodate the different trajectories of guide tube 15 and actuating tube 17 as shown in FIG. 21. At the same time, extension spring 19a can take up some tension load to be able to pull guide tube 15 when retracting.

Figure 22:
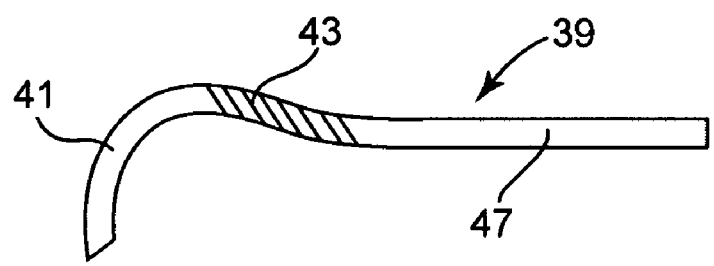
FIG. 22 is a schematic view of an exemplary monolithic arcuate guide tube and actuating tube structure having a flexible region therebetween.

In yet another exemplary embodiment of the present invention, guide tube 15, extension spring 19a, and actuating tube 17 can be combined into one single monolithic body 39 as shown in FIG. 22. Body 39, as shown, comprises an arcuate portion 41, flexible region 43, and a linear region 47. Body 39 may comprise, for example, a tube made of a flexible material, such as stainless steel or a superelastic material. One end of the tube can be bent or shaped so that the whole tube is generally shaped like the collective shape of elements 15, 19a, and 17. In this embodiment, flexible region 43 can be made by machining slits in the corresponding location of extension spring 19a in the collective shape of elements 15, 19a, and 17. The slits can be provided, for example, by laser machining or electrical discharge machining (EDM). In this way, this section of the structure would be relatively flexible, thereby functioning in a similar manner as extension spring 19a discussed above.

In addition, the cutting end of the cable preferably includes one or more cutting edges configured to improve the cutting action by reducing the cutting force on the cable, thereby allowing the cable to cut straighter. FIGS. 10a-10d illustrate exemplary configurations that can be used for the tip of a cable drill in accordance with the present invention such as the cable drill 5 (FIG. 1) and cable drill 32 (FIG. 8), for example. In particular, FIG. 10a illustrates a trochar tip 34 that includes plural, such as three or more, cutting surfaces or edges that are inclined relative to each other; FIG. 10b illustrates a squared tip 36; FIG. 10c illustrates a wedge-shaped tip 38; FIG. 10d illustrates a spade-shaped tip 40. In one embodiment of a trochar tip, a three-sided tip is provided with the ground surfaces being oriented between 13 and 15 degrees from the cable axis, although angles that are larger or smaller than these are contemplated by the present invention.

When drilling through a composite material comprising material with different mechanical properties (such as human or animal bone which is composed of soft cancellous bone and hard cortical bone), a cable drill can tend to deflect as the cable crosses the boundary from the softer material to the harder material. The tendency of the cable drill to deflect is influenced by the amount of axial resistance (cutting force) the cable drill encounters from the material the cable drill is drilling. Thus, in accordance with the present invention, with a certain feed rate (i.e., rate of advancing the cable drill along its length), the cutting force on the cable drill decreases as the rotating speed of the cable drill increases. In order for the cable drill not to deflect as the cable drill crosses the boundary from the softer material to the harder material, the cable drill must be rotated at a speed high enough so that the cutting force the cable drill encounters in the harder material is low enough for the softer material to support the length of cable drill trailing behind the cutting end. This will provide a relatively straight drilling direction. If the cutting force is too high, the softer material will not be able to support the cable drill and keep it straight.

While the parameters for drilling can vary widely depending on the device used (e.g., speed, cable drill dimensions and material properties, and the like), in one exemplary procedure of drilling through cancellous and cortical bovine bone with a particular device, the rotating speed is preferably sufficient for the cutting force on the cable drill to be relatively low, e.g., approximately 0.2 lb (0.9 N), or at least less than 0.5 lb (2.2 N), in order to minimize deviation of the cable drill from a desired path (linear, for example) as the cable drill crosses the boundary between the cancellous bone and the cortical bone. Under certain conditions, such as a high cutting force the cable drill may not be able to drill through the bone along a desired path. Exemplary parameters that can be used for drilling in accordance with the present invention include a rotating speed between approximately 120,000 rpm and 140,000 rpm for distal femoral bovine bone at a feed rate of 1.3 mm/s. For distal tibial human bone, the speed can be between 70,000 rpm and 100,000 rpm at a feed rate of 1.3 mm/s. The desired speed and feed rates may vary for different types of bone or with bone from different animal species and different anatomical locations. The dimension of the cable drill as well as the configuration of the strands of the cable drill and other properties may also have an effect on the optimal cutting speed and feed rate.

In order for the cable drill to follow a desired trajectory at which the cable drill is directed (perpendicular to an intramedullary nail, for example), there is preferably no gap between the material the cable drill is drilling and the arcuate guide tube. Any gap between the arcuate guide tube and the material being drilled is preferably minimized (e.g., less than about 2 mm). Preferably there is minimal play between the cable drill and the inner diameter of the end portion of the arcuate guide tube (around 2 mm from the end where the cable drill exits).

Figure 12:
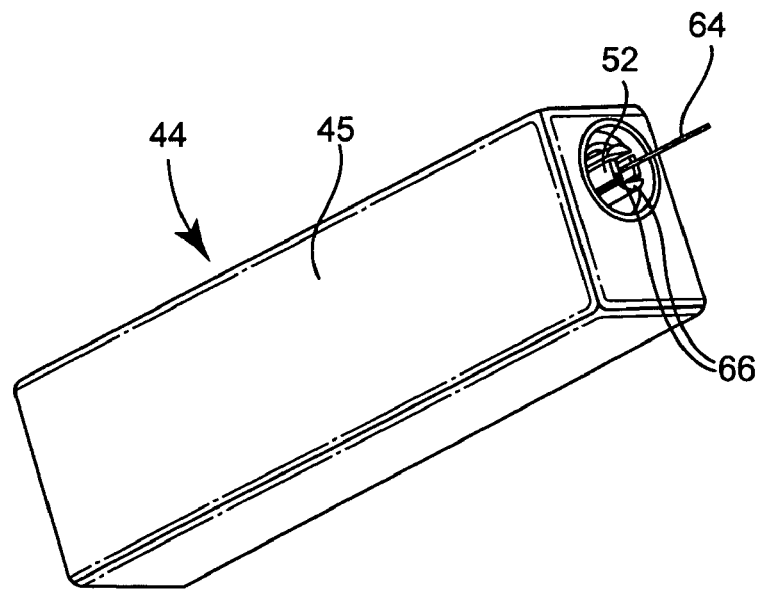
FIG. 12 is another perspective view of the cable drill drive of FIG. 11 showing in particular a disposable drive coupling in accordance with the present invention.
Figure 13:
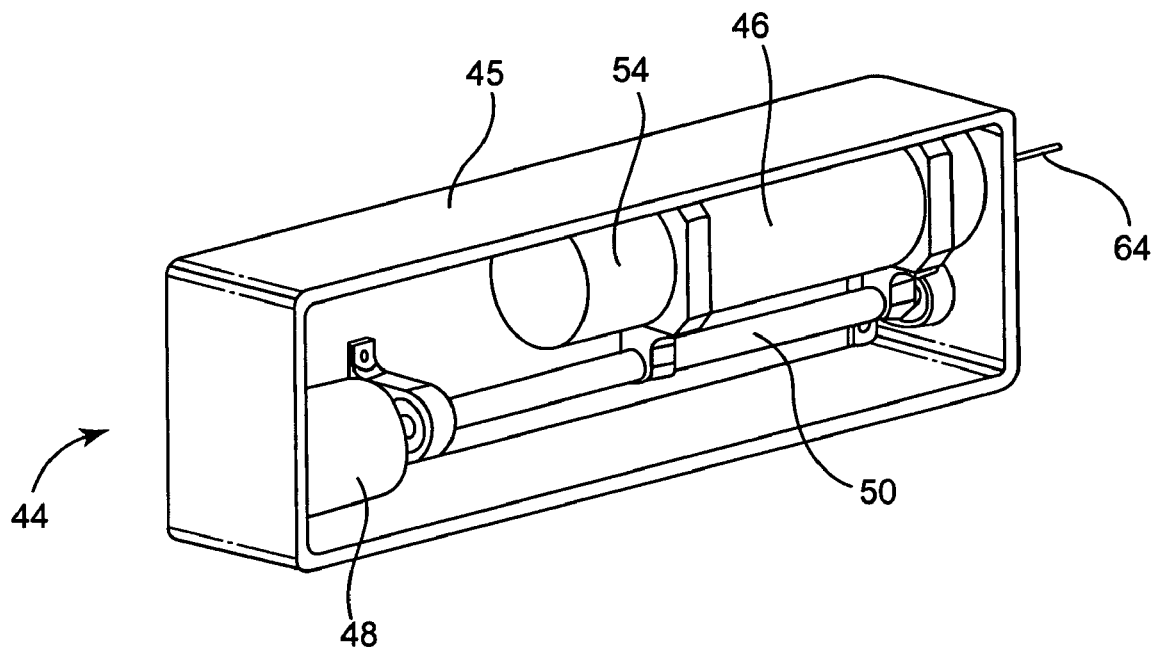
FIG. 13 is a perspective view of the cable drill drive of FIGS. 11 and 12, showing in particular first and second motors and a lead screw positioned within a housing of the drill drive.

FIGS. 11 and 12 illustrate an exemplary cable drill drive 44 of the present invention. Cable drill drive 44 can be used as a source of rotary power for the drilling devices described above. Cable drill drive 44 also functions to advance (and retract) a cable drill along a desired drilling path. FIGS. 13 and 14 show the components inside the drill drive 44 and generally include a housing 45, a main drive 46, a feed motor 48, lead screw 50, and a disposable drive coupling 52.

Figure 15:
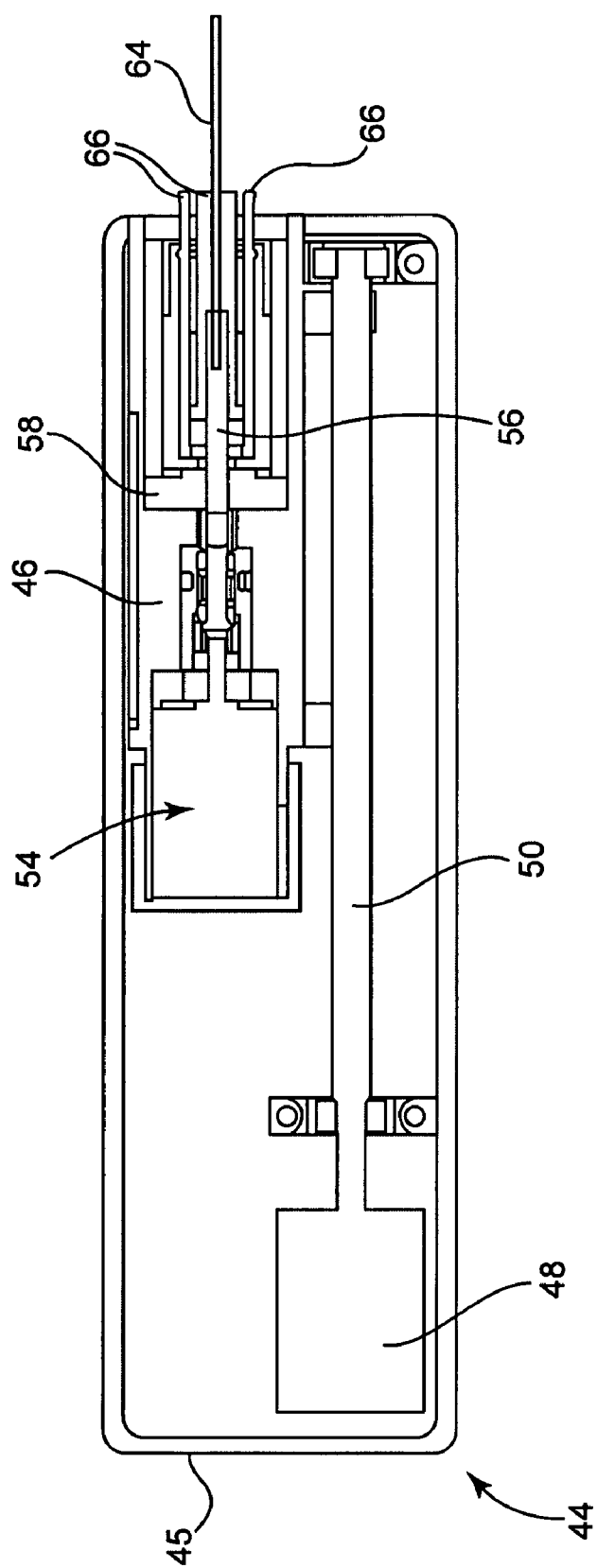
FIG. 15 is a cross-sectional side view of the cable drill drive shown in FIGS. 11 and 12.
Figure 16:
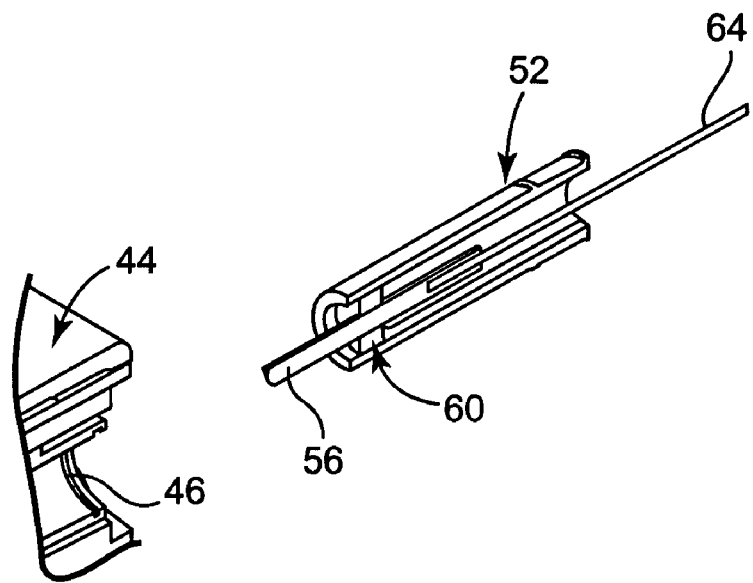
FIG. 16 is a cross-sectional perspective view of an exemplary disposable drive coupling used for coupling a flexible drill with a drive motor of the drill drive in accordance with the present invention.
Figure 17:
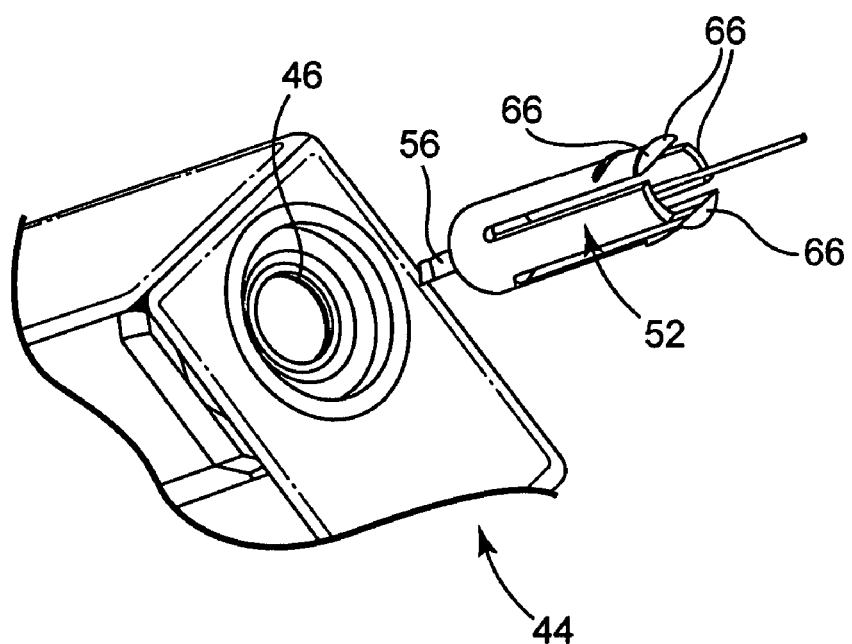
FIG. 17 is a perspective view of an end of the drill drive of FIGS. 11 and 12 showing in particular a receiver for a disposable drive coupling.

FIG. 15 more specifically illustrates the components inside the main drive 46. The main drive 46 contains a high-speed brushless DC motor 54 that drives the shaft 56 in the disposable drive coupling 52. Main drive 46 also contains a load cell 58 that is used for sensing overload conditions. The disposable drive coupling 52 is coupled to the load cell 58 so that substantially all of the axial forces experienced by the shaft 56 are transmitted to the load cell 58. The disposable drive coupling 52 contains a bearing 60 and shaft 56 that couples a tube 64 to the motor (see FIG. 16). The cable (not shown) is attached (e.g., via an adhesive or other means) inside the cavity of the tube 64 so that a length of cable extends beyond the tube 64. This tube 64 telescopes with a larger tube in the retractable curved guide tube assembly. To couple the disposable drive coupling 52 to the main drive 46, resilient fingers 66 of the disposable drive couple are pressed toward the longitudinal axis of the disposable drive coupling 52, and the disposable drive coupling 52 is then inserted into the main drive 46 and the fingers are released to lock the disposable drive coupling 52 in the main drive 46.

Figure 18:
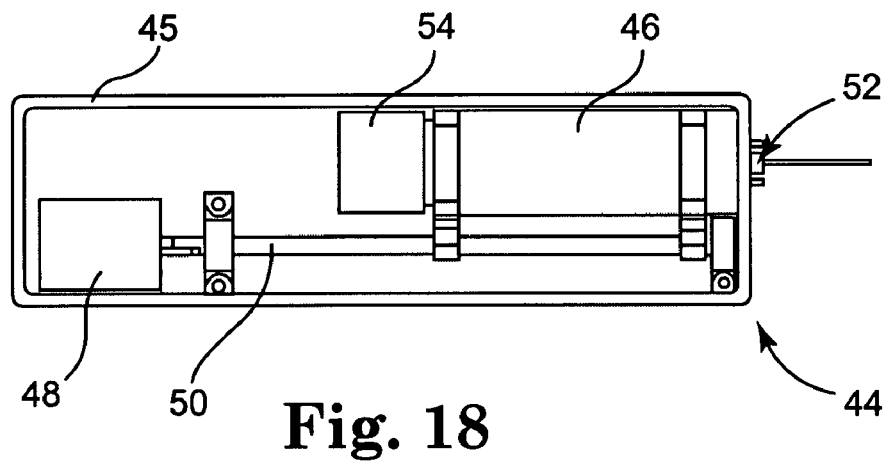
FIG. 18 is a side view of the drill drive of FIGS. 11 and 12 showing the main drive coupled with the disposable drive coupling and in an extended position.
Figure 19:
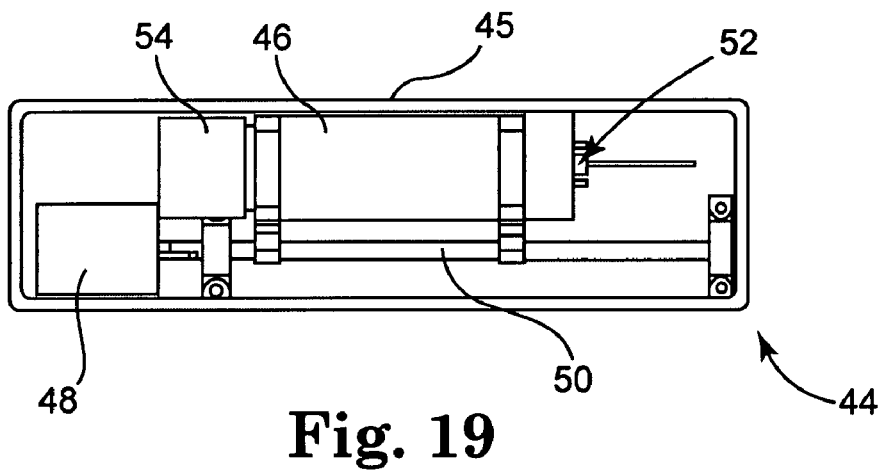
FIGS. 19-20 are side and perspective views, respectively, of the drill drive of FIGS. 11 and 12 showing the main drive coupled with the disposable drive coupling and in a retracted position.
Figure 20:
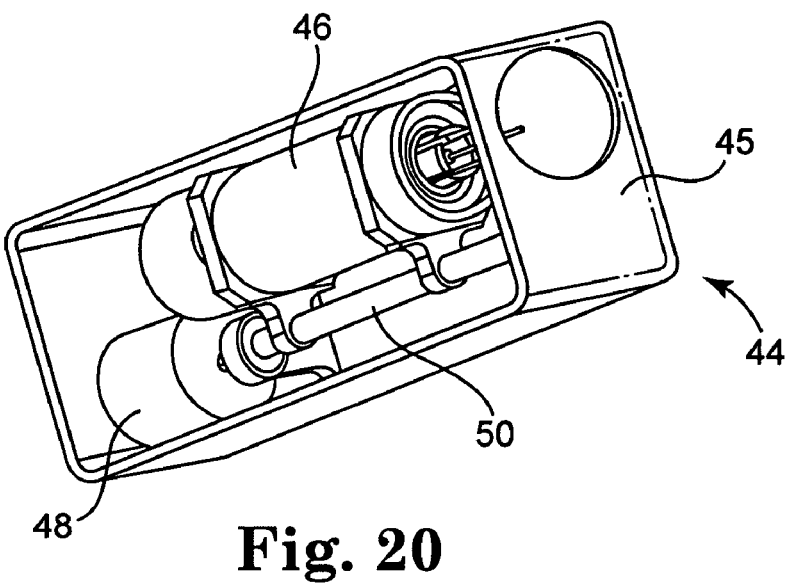

The feed motor 48 drives lead screw 50, which translates the main drive 46 forward and backward at a predetermined feed rate. The two motors are controlled by a control unit (not shown) based on user input as well as inputs from the load cell 58. A control unit may be a distinct unit separate from the cable drill drive 44 or may be integrated into cable drill drive 44. Cable drill drive 44 optionally includes limit switches (not shown) that can be used to provide a signal that indicates a stroke endpoint to a control unit. At the start of an exemplary procedure, the main drive 46 is moved forward and the disposable drive coupling 52 inserted as shown in FIG. 18. The main drive 46, with disposable drive coupling 52, is then retracted as shown in FIG. 19. FIG. 20 shows another exemplary view of the retracted position of the main drive 46. A cable drill (not shown) is then inserted into the guide tube assembly inside an intramedullary nail (if not pre-inserted). The control unit then preferably initiates the drilling sequence when the user activates a start button or other mechanism. At the end of the drilling procedure, the motors preferably stop automatically as controlled by the control unit. The motors will also preferably stop if at any time during the procedure the load cell 58 detects an overload condition that could break the cable drill. Optional forward and backward manual switches can also be incorporated into the cable drill drive 44 and/or control unit to be used for attaching the disposable drive coupling 52.

One exemplary drilling sequence of the present invention that can be followed by using a drill drive of the present invention is described relative to FIG. 19. In the retracted position of the main drive 46, the main drive 46 can be rotated at a preset rpm (e.g., approximately 90,000 rpm). The main drive 46 can then be advanced at a constant rate of 1.3 mm/s, for example. At this rate, the main drive 46 is advanced until a limit switch (not shown) is activated signaling the end of the stroke of a predetermined length (e.g., 2 inches). If at any time during the procedure, the load cell 58 detects a load above a predetermined level (e.g., 0.5 lb), both the main drive motor 54 and the feed motor 48 are stopped automatically and an LED preferably blinks signaling an error. If this happens, the user typically needs to replace the cable and guide tube assemblies and try to drill again. This sub-sequence may be installed as a precautionary measure to prevent cable breakage if the cable minimally advances or does not advance through the bone. All of these described steps can be controlled electronically through a control unit programmed to follow these steps.

Although the description provided above is directed primarily to procedures that involve drilling into bone, the same concepts are equally intended to be applicable to other tissues and body structures, such as cartilage, skin, muscle, fat, and the like. In addition, combinations of any of these various structures with each other and/or in combination with bone structures are intended to be encompassed by the descriptions provided herein.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A surgical drilling device comprising:
a housing defining a first arcuate channel, a second elongate channel and a third elongate channel positioned adjacent said second elongate channel;
a retractable guide tube assembly comprising an arcuate guide tube slidingly positioned in said first arcuate channel defined by the housing, the arcuate guide tube operatively connected to an actuating rod slidingly positioned in said second channel defined by the housing wherein the actuating rod controllably advances the arcuate guide tube from the housing and retracts the arcuate guide tube into the housing; and
a flexible cable drill having a first distal portion slidingly positioned in the arcuate guide tube and a second proximal portion slidingly positioned in said third channel of the housing.

2. The surgical drilling device of claim 1, wherein the connection between the arcuate guide tube and the actuating rod comprise a flexible connection.

3. The surgical drilling device of claim 2, wherein the flexible connection comprises a cable.

4. A surgical drilling device comprising:
a surgical drilling device housing comprising an internal channel having a first arcuate portion and a second linear portion;
a retractable guide tube assembly comprising an arcuate guide tube slidingly positioned in the arcuate portion of the channel of the housing, an end of the arcuate guide tube operatively connected to an end of an actuating tube slidingly positioned in the linear portion of the channel of the housing, wherein the arcuate guide tube is controllably advanceable from the housing and retractable into the housing; and
a flexible cable drill having a cutting end and having a first portion slidingly positioned in the arcuate guide tube and a second portion slidingly positioned in the actuating tube.

5. The surgical drilling device of claim 4, wherein a leading edge of the arcuate guide tube comprises a sharpened region.

6. The surgical drilling device of claim 4, further comprising a motor operatively connected to the cable drill.

7. The surgical device of claim 4, further comprising an advancing device for controllably advancing the cable drill in a drilling direction.

8. The surgical device of claim 7, further comprising a control system.

9. The surgical drilling device of claim 4, wherein the cutting end of the cable drill comprises a trocar tip.

10. The surgical drilling device of claim 4, wherein the cutting end of the cable drill comprises a chisel tip.

11. The surgical drilling device of claim 4, wherein the connection between the arcuate guide tube and the actuating tube comprises a flexible connection.

12. The surgical drilling device of claim 11, wherein the flexible connection includes one or more hinges.

13. The surgical drilling device of claim 11, wherein the flexible connection comprises a spring, a woven sleeve, a rubber sleeve, slits formed in the arcuate guide tube, or a plastic sleeve.

14. The surgical drilling device of claim 11, wherein the arcuate guide tube and the actuating tube together comprise a monolithic structure and the connections between the arcuate guide tube and the actuating tube comprises a flexible region integral with the monolithic structure.

15. The surgical drilling device according to claim 4, further comprising:

a drive system housing;
a drive motor that is translatable along a linear path relative to the housing;
a disposable drive coupling having a drive shaft releasably coupled with the drive shaft of the drive motor; and
a load cell operatively positioned relative to the disposable drive coupling for sensing axial forces acting on the drive shaft of the disposable drive coupling.

16. The surgical drilling device of claim 15, wherein the drive motor is advanced at a controlled rate in order to advance the drill in a surgical drilling device.

17. The surgical drilling device of claim 4 wherein said arcuate guide tube comprises a superelastic material.

18. The surgical drilling device of claim 4 wherein said arcuate guide tube comprises stainless steel.

* * * * *